United States Patent
Di Bartolomeo

(10) Patent No.: US 7,524,512 B2
(45) Date of Patent: Apr. 28, 2009

(54) COMPOSITION AND METHOD FOR THE PREVENTION AND RELIEF OF THE SYMPTOMS OF AN INCOMPETENT OR PATULOUS EUSTACHIAN TUBE

(76) Inventor: Joseph R. Di Bartolomeo, 2420 Castillo St., Suite 100, Santa Barbara, CA (US) 93105

( * ) Notice: Subject to any disclaimer, the term of this patent is extended or adjusted under 35 U.S.C. 154(b) by 0 days.

(21) Appl. No.: 11/777,550

(22) Filed: Jul. 13, 2007

(65) Prior Publication Data

US 2009/0017098 A1  Jan. 15, 2009

(51) Int. Cl.
*A61M 5/00* (2006.01)
*A61M 31/00* (2006.01)
*A61M 39/00* (2006.01)
*A61K 31/375* (2006.01)
*A61K 9/00* (2006.01)
*A61P 27/16* (2006.01)

(52) U.S. Cl. .................. 424/437; 424/400; 514/474; 604/11; 604/19

(58) Field of Classification Search ................ 514/474
See application file for complete search history.

(56) References Cited

U.S. PATENT DOCUMENTS

| | | | | |
|---|---|---|---|---|
| 4,826,683 | A * | 5/1989 | Bates | 424/641 |
| 5,421,818 | A * | 6/1995 | Arenberg | 604/21 |
| 5,470,587 | A * | 11/1995 | Di Bartolomeo | 424/661 |
| 5,508,282 | A | 4/1996 | Tulin-Silver et al. | |
| 6,878,691 | B2 | 4/2005 | Or et al. | |
| 2004/0204471 | A1 | 10/2004 | Seibert | |
| 2005/0065115 | A1 * | 3/2005 | Bassiri et al. | 514/64 |
| 2006/0147492 | A1 | 7/2006 | Hunter et al. | |

FOREIGN PATENT DOCUMENTS

JP   08119875 A  *  5/1996

OTHER PUBLICATIONS

Balch, Phyllis A., Ascorbic Acid Flush, Prescription for Nutritional Healing, 3rd ed, Part Three, p. 697, Avery, Oct. 19, 2000.
Yamaguchi, Tadashi, "Pathology of the Typmpanic Mucosa with Chroinc INflammation with Reference to Vitamin C Metabolism", Nippon Jibiinkoka Gakkai Kaiho (Sep. 1972: vol. 75, pp. 905-917) Cover letter and summary translation dated Oct. 5, 2005 by Isamnu Sando, M.D.
Yigit, Ozgur et al, "The effect of topical ascorbic acid applications on the healing of rat tympanic membrane perforations", Kulak Burun Bogaz Ihtis Derg, 11(1): 1-4, 2003.

* cited by examiner

*Primary Examiner*—Sreeni Padmanabhan
*Assistant Examiner*—Sahar Javanmard
(74) *Attorney, Agent, or Firm*—Felix L. Fischer

(57) ABSTRACT

A composition and methods for the treatment of symptoms due to disorders, disease or trauma that impairs normal function of die Eustachian tube and alters vital structures or tissues of the middle ear. This includes diseases and disorders of the Eustachian tube altered by tubal incompetence, inflammatory phenomenon as rhinitis, nasal allergies, infections by microorganisms, tympanic membrane rupture or trauma and variants. The composition is comprised of solution including L-Ascorbic acid and a pharmaceutically acceptable liquid carrier and delivery system. The administration of which is applied topically in appropriate composition and dosage for intranasal or trans tympanic route in the form of drops, spray, aerosol, rinse, douche, gel, or devices.

21 Claims, 1 Drawing Sheet

COMPOSITION AND METHOD FOR THE PREVENTION AND RELIEF OF THE SYMPTOMS OF AN INCOMPETENT OR PATULOUS EUSTACHIAN TUBE

FIELD OF THE INVENTION

This invention relates generally to treatment of middle ear disorders and more specifically to a composition and treatment protocol for treatment of patulous Eustachian tube disorders of the middle ear and otitis media.

BACKGROUND

The Eustachian tube (ET) is an adnexa structure in the middle ear in man. It is a very narrow air passage in the wall of the middle ear which connects it to the nasopharynx, —a midline air filled space in the back of the nose. It is approximately 37 mm long and is slightly hour-glass shaped, flattened anterior-posteriorly. The small lumen of the eustachian tube permits the exchange of ambient gases between the middle ear and nasopharynx and the transport of middle ear secretions into the nasopharynx. The lateral one-third of the Eustachian tube (tympanic segment) is made of bone, while the medial two-thirds (pharyngeal segment) is cartilaginous. A constriction at the junction of the bony and cartilaginous segments, called the isthmus, may be as narrow as 1.0 mm by 1.5 mm. This tube regulates the intermittent exchange of air to or from the middle ear space to maintain equal pressure on both sides of the eardrum. The surface of the epithelium of the middle ear and eustachian tube is covered by a raucous blanket which is a defensive barrier against inhaled pollutants and a multitude of microorganisms. Middle ear secretions are normally eliminated through the ET.

In man, the Eustachian tube is a very unique structure that enables the middle ear pressure to adapt to various altitude changes and, and when closed it prevents the endogenous intraoral sounds of respiration and vocalization from reaching the middle ear to compete with and mask out the environmental sounds for reception and relay to the inner ear.

Normally, the Eustachian tube maintains an isobaric relationship between the middle ear space and the ambient air exchanged within the nasal passages during breathing. The critical opening pressure for the tube to ventilate the middle ear chamber is related to the surface tension and diameter of the ET opening onto the lateral wall of the nasopharynx. This is modified by the rheologic properties of the mucus blanket on the endothelial tissues. In its natural state, the Eustachian tube orifice is always closed, but may actively open spontaneously several times a minute or when swallowing or yawning. As integral part of the middle ear, the Eustachian tube functions to prevent and ameliorate the same inflammatory diseases such as otitis media etc. and its complications.

Incompetent Eustachian tube disorders refer to those conditions in which the closure of the facet at the orifice does not occur due to an increase in the diameter of the lumen of the Eustachian tube, a change in the surface tension of the secretions or fluid covering the mucous membrane, or a failure of the normal cartilage valve mechanism to passively relax for normal closure.

In this small sub set of individuals the Eustachian tube lumen is abnormally open continuously or intermittently. While the tube is open, it allows the respiratory sounds and speech of an individual to pass directly through the patent Eustachian tube to the middle ear sound-receiving mechanism. These individuals are very uncomfortable and frequently complain of a paradoxical symptom of a "clogged, plugged or stuffy ear" or a crackling or squeaking sound in actuality, there is a failure of the facet of Eustachian tube valve to passively collapse and seal the entrance at the nasopharynx. When they deny having a respiratory infection, further questioning may elicit a complaint of autophony (hearing their own breath sounds amplified in one's ear) and of hearing amphoric sounds in their ear similar to the sound of air being blown across the mouth of an uncapped empty bottle, or their voice sounding loud or strange. The symptom of autophony is pathognomonic of a patulous Eustachian tube disorder of the middle ear.

While the Eustachian Tube remains open, the continuous free flow of air from each respiration or vocal effort rushes to the middle ear causing the tympanum to resonate loudly. This uncontrollably amplifies the endogenous sounds (autophony) in one's ear. These forceful air currents, or acoustical energy, produced by breathing and vocalization generated within the approximate voice box, impact directly through the open Eustachian tube to the sensitive sound transmission system of the middle ear producing disturbing sounds and acoustical energy.

Unlike the symptoms of a common cold, PET symptoms totally disappear when lying down due to a shift of body fluids to the head increases local edema and passive closure of the tube. And so, to maintain closure, some patients spend the their day time hours supine, in bed.

The symptom of autophony—hearing the disturbing loud sounds from one's own breathing and voice, may be so disabling that many patients have considered suicide, and some attempts have been successful.

The patulous Eustachian tube syndrome and less severe variants such as a Patent, open, hyper-patent or semi-patulous Eustachian tube are variants of Eustachian tube incompetence.

In the past, different remedies have been recommended for the patulous Eustachian tube syndrome. These include sitting, and then bending over with ones head between the knees to increase nasal edema. Treatments included nasal insufflation of boric acid-salicylic acid power, local application of liquid silver nitrate, diathermy, Premarin hormonal or saturated solution of iodine (SSKI) drops. Another therapy has employed Kamikihi-To as reported by Jia-Wei-Gui-Pi-Tang. Some were impractical. None of these treatments have been consistently successful, nor are they without side effects, or serious complications.

In the inventor's previous related U.S. Pat. No. 5,470,587 (Nov. 28, 1995) which is herein incorporated by reference, the principle embodiment included hydrochloric acid (HCl), an inorganic acid. The invention sited above stimulated the necessary local edematous response to close the tube with the immediate, but short term, relief of symptoms due primarily to its pH effect. The properties of the novel invention and novel method of administration described herein stimulate both the immediate edema and the products essential for tissue healing, namely, dermatofibroblasts and pre-collagen fibers.

Surgical procedures have been advocated, including the injection of paraffin, Teflon, collagen, or Gelatin sponge injection into the wall around the Eustachian tube opening. Invasive surgery involving pterygoid hamulotomy has been performed or occlusion of the Eustachian tube lumen by a plug. Diathermy probe therapy has been used on the past. Laser-assisted endoscopic surgery or autologous fat grafting has been recommended for severely debilitating cases.

Additionally, among children in the US, 35 to 85 percent experience middle ear disease from otitis media in the first six months of life. Acute ear infections account for 15 to 30 million visits to the doctor each year in the U.S. In fact, ear infections are the most common reason why an American child sees the doctor. This is probably the result of prenatal deficiencies, and the infant or child's exposure to secondary smoke and respiratory viruses when their immune system is not fully developed.

Certain bacteria are reported to be the primary causes of acute otitis media (AOM) and are detected in about 60% of cases. The bacteria most commonly causing ear infections are: Streptococcus pneumoniae (also called S. pneumoniae or pneumococcus), the most common bacterial cause of acute otitis media, causing about 40% to 80% of cases in the U.S.; Haemophilus influenzae, the next most common culprit and is responsible for 20% to 30% of acute infections; and Moraxella catarrhalis, also a common infectious agent, responsible for 10% to 20% of Less common bacteria are Streptococcus pyogenes and Staphylococcus aureus.

A serious sequalae of bacterial chronic otitis media includes otitis media with effusion (OME) which is associated with complications such as a ruptured tympanic membrane (TM). The failure of the Eustachian tube to expel or eliminate the natural secretions, microorganisms, biofilms and toxic products result in destruction of the tissues, TM rupture and hearing loss. When the fluid becomes infected the increased pressure is very painful and causes the delicate tympanic membrane to rupture releasing the toxins into the external ear canal for elimination The ideal treatment should involve a product that is first safe and free of side effects, non-toxic, exhibit high potency at a pH that facilitates host tissue defenses while at the same level is detrimental to the reproductive cycle of most microorganisms, and the biochemical or physical property to break down the protective biofilm barrier surrounding the microorganism or toxins. It would be advantageous if embodiment has anti oxidant properties to reduce free radical toxins on the damaged host tissue and participate in the production of the essential ingredients (pre-collagen) to complete the healing process of the tissue and improved function.

In the past, antibiotics have been the mainstay of eliminating bacterial microorganisms by direct biochemical interaction. Antibiotics can only treat the infection when and if the agent is capable of penetrating the biofilm barrier and altering the biochemistry of the microorganism internally. This is seldom the case now.

Of note, about 15% of these bacteria are now believed to be resistant to the first-choice antibiotics. With the overuse of antibiotics and the development of resistance by microorganisms, such treatment has become less effective and frequent side effects have become common.

More recently, because the chemical structure of the newer anti-infective agents are more complex, antibiotics are not absorbable in the gastrointestinal tract, necessitating that the medication be administered by intravenous injection which is further associated with serious side effects such as ototoxicity, hearing loss and tinnitus, allergic reactions. Scientific studies have identified prenatal markers, such as smoking, that predispose the infant to develop middle ear infections. Among the prenatal risk factors for early Otitis Media (OM) that can be modified, mother's intake of vitamin C and alcohol during pregnancy could have future health implications. Alcohol may stimulate the fetal liver to produce metabolic enzymes which degrade vitamin C producing deficiencies in both the fetus and the infant. Vitamin C—deficient animals have neutrophils with reduced bactericidal activity and ascorbic acid may also play a role in the fetal development of cartilage, bone, and the muscle of the Eustachian tube.

Recent discoveries have identified a universal mechanism by which disease is transmitted, established, perpetuated and flourishes despite antibiotic therapy. This is through the protective covering of biofilm. The organic matter adheres to the surface target organ and shields the penetration of the external membrane of the microorganisms by many forms of chemotherapy. To be effective, it is necessary the therapeutic agent to break down the biofilm, and then inactivate the microorganisms by establishing a pH environment which is detrimental to their survival.

The relative acidity of a solution or tissue is measured according to a pH scale that ranges from 0-14. Those registering above 7 function within an alkaline environment, those below 7 are acidic. A solution with a pH of 7 is considered neutral. The mathematical symbol pH represents the logarithm of the reciprocal of the hydrogen-ion concentration in gram atoms per liter of solution. The level of the pH regulates the biochemical availability of nutrients for the chemical processes of all vital tissues to survive.

It is therefore desirable to provide a composition for the treatment of the fundamental pathologic processes antecedent to patulous Eustachian tube disorders and to the dysfunctional tubal stenosis in middle ear diseases by employing an effective, non-toxic composition with known co-enzymatic and vital tissue healing properties.

SUMMARY

The embodiments of the invention disclosed herein provide a novel formulation and method for the prevention and relief of symptoms of inflammatory disease or functional disorders of the middle ear adnexa, the Eustachian tube, manifested by autophony or tubal tinnitus due to a severe form of Eustachian tube incompetence, patulous Eustachian tube syndrome, or deformity, acquired or following surgery, radiation or trauma. The inventive composition and method are further effective for the prevention and relief of symptoms related to primary inflammatory disease or functional disorders of the middle ear or such as may occur secondary to allergy, rhinitis or sinusitis, microorganisms, structural deformities or tubal dysfunction.

A method of treating the patulous Eustachian tube syndrome, and variants of Eustachian tube incompetence, includes the steps of: applying to a person's nasal mucosa a composition of at least of L-Ascorbic acid, with a pH level in the range of about 2.0 pH to about 2.5 pH, and a pharmaceutically acceptable liquid carrier and delivery system, the L-Ascorbic acid in the carrier at a concentration form about 25% to about 4% wt./volume.

A method of preventing and treating Middle Ear Diseases including Otitis Media (OM), Otitis media with effusion (OME), Tympanic Membrane (TM) or Eustachian Tube (ET) due to dysfunction or associated with allergy, rhinitis, sinusitis, and inflammatory disease from toxins, microorganisms, the biofilm and abiotic adhesin co-factors coating the surface of implanted devices, including the steps of applying a composition comprised of L-Ascorbic acid at a pH in the range of about 2.3 pH to 4.0 pH level in a pharmaceutically acceptable liquid carrier at a concentration from about 10. % to about 0.01%, wt./volume to the middle ear through the natural tubal stoma, an acquired opening or implants, to prevent or treat middle ear disease and its sequalae.

BRIEF DESCRIPTION OF THE DRAWINGS

The embodiments of the invention described herein are further described with reference to the figures wherein.

DETAILED DESCRIPTION

Figure 1:
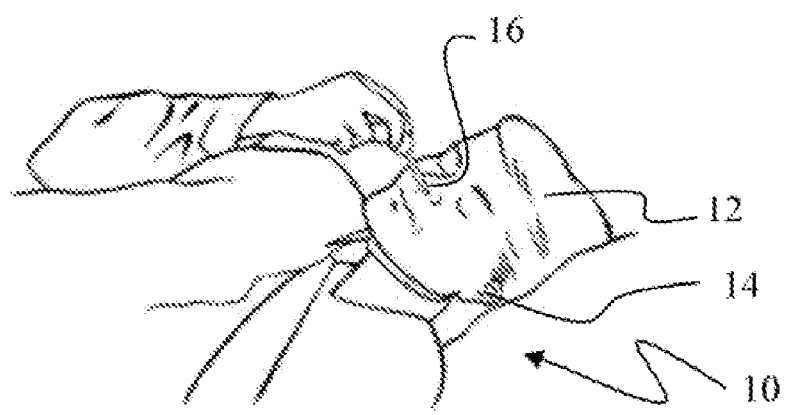
FIG. 1 is a view of a patient, employing the Di Bartolomeo position or Tubal position for administration of drops according the present invention in the left ear.

The embodiments described herein for the invention provide that when L-ascorbic acid is dissolved in an aqueous solution, the pH of that solution decreases sharply due to the dissociation of the hydrogen ion from the enediol group. The main contribution to the lowering of pH is the hydroxy group located on the number 3 carbon (C3). This composition provides a more flexible therapeutic pH range than HCL, is much safer, has no known toxicity, and is necessary for the production of collagen to support the strength and healing of these tissues. Unfortunately, man is unable synthesize L-Ascorbic acid due to the absence of the biochemical step in the liver of the species to convert L-gulonolactone which is required for the biosynthesis of L-ascorbic acid. Therefore, in man, the composition provided by the embodiment includes exogenous L-Ascorbic acid, an essential nutrient for tissue health. Further the embodiments of the composition and the methods described assure the availability of the composition directly to the tissue in obvious need.

The composition of the first exemplary embodiment has known antioxidant properties, scientifically established, that combat the build up of metabolic wastes. It restores the defensive bioactive reactions such as surface tension lowering substance (STLS) to combat the adherence or biofilm products of microorganisms.

Because man cannot synthesize ascorbic acid, it is a recognized essential nutrient that has to be provided by an exogenous source as referenced in [At this time, the Food and Nutrition Board of the U.S. National Research Council recommends a daily allowance of 60 mg in a 70 kg man to support certain vital functions.

The exemplary first embodiment employs this essential nutrient in the therapeutic form required by man for the production of pre-collagen necessary for the strength and healing process of the tubal tissues.

Unfortunately the early symptoms of PET may include those similar complaints that appear similar to those reported with the common cold, tubal stenosis, otitis media, environmental allergies, rhinitis or sinusitis. But in PET the fundamental cause is an OPEN TUBE, contrary to the inflammatory obstructive phenomenon of the middle ear congestion from a common cold etc. Therefore, it is essential to determine the exceptional diagnosis of PET and select the contrary therapy to relieve the disturbing cardinal symptoms of autophony. For anyone to recommend any of the conventional medications or non prescription decongestant remedies because of a misdiagnosis, it will invariably make the PET symptoms much worse.

OPERATION OF THE FIRST EXEMPLARY EMBODIMENT

The Patulous Eustachian Tube is abnormally open throughout the day when the individual is upright and about. The lumen of the tube remains open and the phenomenon of autophony, hearing one's amplified breath sounds and voice disturbingly loud, will persist throughout the day.

A novel composition for ameliorating patulous Eustachian tube symptoms, is provided by a solution of L-Ascorbic acid and a pharmaceutically acceptable liquid carrier in therapeutically effective amounts to normalize the surface tension of the luminal tissues of the eustachian tube, the solution having a pH level in the range of about 2 to 2.5 pH. The L-Ascorbic acid or comparable ingredient is in the form of U.S.P. grade, extra pure fine powder, granular powder or pure crystals. The L-Ascorbic acid employed in the embodiment is also known as Vitamin C, hexuronic acid, an antisorbutic vitamin, with chemical formula $C_6H_8O_6$ and a molecular weight of 176.12, or its derivatives: Ester-C, Ascorbate, L-xyloascorbic acid, 3-oxo-L-gulofuranolactone, L-3-keto threo hexuronic acid lactone, or oxidation forms: dehydro-L-ascorbic acid, hydrophobic ascorbic acid, or 2-O-.alpha-D-glocopyranosyl-L-Ascorbic acid. For their synergistic effect to enhance the properties of the novel composition, specific antioxidants may be added. These include the flavon antioxidant, bioflavonoid, and the nutrient antioxidant, water solubilized vitamin E (alpha-tocopherol) and zinc salt(s) added to the L-Ascorbic acid composition.

For an exemplary embodiment, the liquid carrier is distilled water and the solution has a pH level in the range of about pH 1.9 to a pH of about 3.9. The L-Ascorbic acid is present in the carrier at a concentration from about 2% to about 25% wt./volume. The pH of Ascorbic acid produces the desired edema, as an immediate effect but also has co-enzyme and bioactive properties to combat the inflammatory reaction and facilitate the healing process.

A novel method to prevent or ameliorate the serious symptoms of middle ear disease due to impairment of its Eustachian tube function is accomplished by applying the composition through the natural orifices, or acquired openings, or implanted devices to normalize Eustachian tube function.

The solution is topically applied to the nasal mucosa, however in alternative embodiments of the method protocol, the solution is applied to the middle ear chamber mucosa. For application to the nasal mucosa, the solution is applied in drops into the nose, as a spray into the nose or in an aerosol into the nose. In one application, the solution is applied via an ET catheter to the nasopharyngeal stoma of the eustachian tube.

For application to the middle ear chamber mucosa, the solution is applied to the middle ear employing a syringe and needle, a tympanic membrane puncture or a myringotomy, by employing an implanted device in the middle ear chamber or bridging the defect of the tympanic membrane of the middle ear chamber.

In an exemplary first administration protocol, the composition is administered in the form of nose drops, the patient sniffs them through the ipsilateral nostril on the side of the symptomatic ear affected with the disorder. The number of drops administered can be titrated to the needs of the individual patient. The patient can sniff from two to four drops of the solution, and the drops are sniffed back into the nostril so as to deliver the medication to the Eustachian tube opening in the back of the nose. Administration of the drops may be repeated again in four to six hours. As desired, the daily dose maybe increased to 4 drops per administration.

The pH of Ascorbic acid produces the desired tubal edema, as an immediate effect but also has bioactive properties to combat the inflammatory reaction facilitating the healing process.

An exemplary nasal drop administration protocol has been developed for the first exemplary embodiment. To achieve normal closure of the lumen, 2-6 drops of the nasal supplement solution are applied to the stoma or opening of the Eustachian tube. It may take two weeks before changes in symptoms become apparent.

PatulEND™ nose drops are designed to increase the edema of the membrane at the stomal entrance of the Eustachian tube to the critical closing pressure level and seal the opening. When drops are instilled into the nasal chamber, they are slowly absorbed upon contact with the surface. It is important to sniff the nose drops so that they are drawn back to the opening of the Eustachian tube where they can be preferentially absorbed at the stoma. After using the supplement for several days one is usually able to master the technique and can identify the sensation associated with proper delivery of the drops to the Eustachian tube area.

Figure 2:
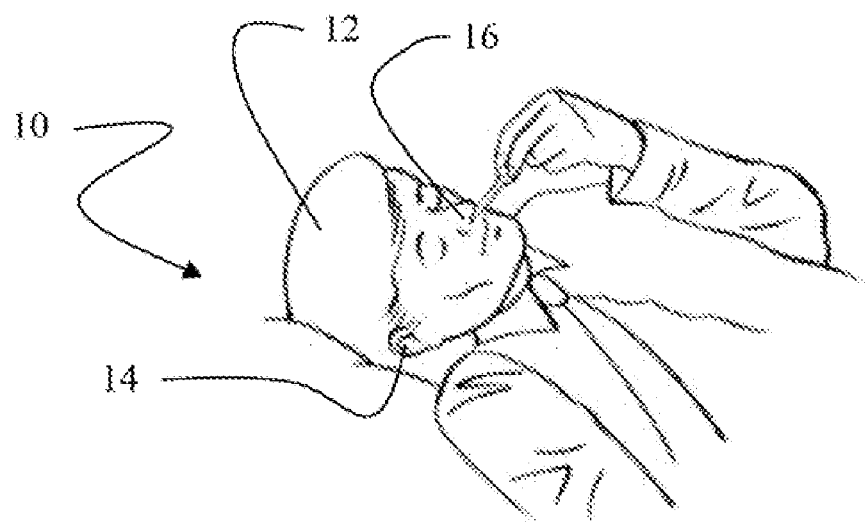
FIG. 2 is a view of a patient employing the Di Bartolomeo position or Tubal position for administration of drops according the present invention in the right ear.

Referring to the illustrations in FIGS. 1 and 2 for reference, after the patient been up for a period of time, symptoms begin as the tubal tissues lose fluid and the lumen increases. When the patient feels the symptom of autophony is about to occur, gently blowing the nose to clear any mucous is accomplished.

With the patient 10 lying with head 12 between 45 to 60 degrees above horizontal. The head is turned 45 to 60 degrees toward the affected ear 14, right as shown in FIG. 1 and left as shown in FIG. 2. This places the Eustachian tube stoma (opening) lower than the nostril 16. Gravity will allow the drops to flow to the back of the nose. Sniffing will draw the drops further info the nasal passage to the Eustachian tube before the semi-permiable membrane lining of the nasal passage can absorb them. Alternatively while sitting in a chair, the head is tilted back at approximately 45 degrees and then tilted toward the affected ear to place it almost below the nose.

For nasal administration, to instill the drops, put the dropper tip one-quarter inch (¼") into the lower nostril (affected side), closest to the symptomatic ear.

Instill 2-4 drops depending on individual anatomy. Sniffing briskly to draws the drops back approximately three inches (3") to the location of the tube opening where they will be absorbed. The patient may feel a brief burning or stinging sensation when the drops are administered properly to stimulate the closure of the stoma of the tube. The patient then remains lying down in the administering position for ten (10) seconds.

The solution in the exemplary embodiment is devoid of pharmaceutical agents, astringent agents, hormones, alcohol, botanicals, yeast, wheat, soy, dairy products, sugar, salt, starch, and artificial coloring or dyes and is formulated without the uses of preservatives, artificial flavors or colors. It is light sensitive and oxygen sensitive.

SELECTED CASE STUDIES

JD: The inventor is a board certified Otolaryngologist in the specialty of diseases of the Ear, Nose and Throat. After 25 years of specialty practice, he was still not able to find a treatment, for his Patulous Eustachian tube patients. By serendipity, he developed a Patulous Eustachian tube himself, his colleagues advised him and their other PET patients to, "learn to live with it, there is no treatment" except for complex surgery with unpredictable results. He submitted an investigational New Drug application (IND) 40,202 under section 505(i) of the Food and Drug Administration and became the principle investigator in the Patulous Eustachain tube study. He offered himself as the first subject to be treated with the early pharmaceutical compositions for analysis of the tissue reactions, efficacy and possible side effects. The study continued with increased enrollment of clinical trial subjects during Phase I, Phase II and eventually Phase III. The inventor was responsible for development of the pharmacological studies of the patulous treatment with relief of symptoms. His investigational research experience resulted in the pharmaceutical composition of the original embodiment under U.S. Pat. No. 5,470,587 (Nov. 28, 1995) which is herein incorporated by reference.

After the active study had entered its tenth years, the inventor continued his research to develop the present non-pharmaceutical Embodiment which is safer and more effective than its predecessor. He has used both products with benefit and relief of his PET symptoms. He finally used only the current drug-free embodiment, as needed. Two drops of L-Ascorbic acid, 15% wt/vol. in distilled water solution, under the method described herein with complete symptomatic relief after one month.

The following examples are set forth to illustrate the exemplary first embodiment.

Example I

A 36-year-old female had a history of autophony which occurred throughout the day several days a week, especially during and after exercise. The patient was treated with the embodiment and methods described using the composition delivered in the form of nose drops applied topically to the nasal mucosa. Three drops of L-Ascorbic acid, 15% wt/vol, in distilled water solution, were sniffed into the nostril on the side of the abnormal Eustachian tube by the novel PET method described herein The drops were taken approximately two hours after arising from sleep, and repeated again six hours later. Excellent results were achieved with the patulous Eustachian tube syndrome completely relieved, and no adverse side effects were noted. The treatment was required intermittently and repeated approximately every two months, as required.

Example II

Semi-patulous symptoms of an incompetent Auditory tube include one's voice resonating loudly, a vibratory sensation in the ear or a complaint of "clogged ears". The symptom is most disturbing to professional singers or lecturers. Image studies may be obtained to ride out a dehiscence of the bone of the superior semicircular canal (SSC) of the inner ear.

A 52-year-old male professional entertainer suffered from a unilateral Semi-patulous Eustachian tube syndrome which occurred approximately two days a week and recurred about three weeks each month, particularly when performing on stage. A composition comprising the exemplary first embodiment of an aqueous solution of L-Ascorbic Acid, 20% wt/vol, in an aqueous solution with a pH of 2.0 for optimal therapeutic effect was administered in a dosage of 2-4 drops for each treatment. The patient sniffed the drops into the ipsilateral nostril by the method of the invention approximately three hours after arising in the morning. This treatment was repeated on subsequent mornings when symptoms were present. The results were excellent in that the autophony symptom of an Incompetent Eustachian Tube receded completely, and there were no adverse side effects.

Example III

A four-year old child had been suffering from chronic otitis media with effusion. The child had been treated with the usual antihistamines, decongestants, and repeated antibiotics. The antibiotics were no longer effective and side effects were beginning to occur and an examination revealed persistent middle ear fluid, bilateral. Tympanometry demonstrated flat tympanograms. The child was treated with politzerization followed by administration of the invention with the composition modified for optimal effect with minimal discomfort. L-Ascorbic acid, 4% wt/vol in physiologic saline delivered employing a metered nasal spray bottle. After two weeks the child began to experience occasional normal "clearing" of his Eustachian and his hearing was restored. In the second week, his hearing improvement was maintained and continued at his pre-ear infection level with no further need for the invention. There were no adverse side effects.

Example IV

A 62 year-old woman with nasopharyngeal carcinoma was treated with wide resection of the lateral nasal pharyngeal wall, sinus and floor of the orbit. The surgery left her with difficulty swallowing, chronic pain, and a patulous Eustachian tube. She stated that she could tolerate the post operative pain and difficulty swallowing but not the continuous autophony through the partially transected patulous Eustachian tube. She was treated with the composition of L-Ascorbic acid, 15% wt/vol in an aqueous solution with a pH of 2.1. By the novel method of Di Bartolomeo described herein. It was self-administered daily in the morning for the next several years. She eventually died because of a primary disease. Cytology studies of the right Eustachian tube area were reported to be free of cancer. There was no carcinogenic effect from the daily administration of her nose drops over several years.

OPERATION OF THE SECOND EXEMPLARY EMBODIMENT

Modification of the composition and methods of treatment for otitis media (OM) and otitis media with effusion (OME) due to inflammatory disease of the middle ear epithelium, structures and specialized membranous tissues is described below. The inflammatory diseases of the middle ear and biofilm are treated herein treated by the following methods. The composition is preferably delivered through the natural opening at the nasopharyngeal orifice of the eustachian tube leading to the middle ear chamber. If this is not possible, a needle or myringotomy incision in made in the tympanic membrane (ear drum) via the external ear canal for the delivery of the embodiment, with or without a device, into the middle ear to chamber. The chamber is irrigated and the biofilm flushed by the exemplary embodiment of the composition delivered as described above.

In otitis media, the solution is topically applied to the Eustachian Tube mucosa in appropriate dosage forms for administration or delivered to the middle ear chamber by delivery through the stoma of the Eustachian Tube in the form of nasal drops, spray, aerosol, rinse, douche or gel. The delivery system may include the modified Politzer technique or catheter insufflation of the middle ear.

If the middle ear chamber is not easily accessible through its natural eustachian tubal stoma, the chamber can be reached directly by surgically penetrating or making an incision in the tympanic membrane of the lateral wall of the middle ear, as in a myringotomy.

In this way, the contaminated middle ear fluid, microorganisms and biofilm adhesins seen in OME may be degraded and removed by a paracentesis (needle)or myringotomy (scalpel) incision of the tympanic membrane with aspiration of the fluid, under direct visualization. The middle ear fluids and debris are degraded and flushed out by rinsing with the composition of the exemplary embodiment delivered through the acquired opening into the middle ear chamber, in the form of nasal drops, spray, aerosol, rinse, douche, irrigation or gel. The composition, L-Ascorbic acid, in about 4% to 10% wt/vol in an aqueous solution, is employed through a surgically made incision or acquired defect in the tympanic membrane of the middle ear for the optimal characteristics or effects to reestablish Eustachian luminal patency, restore the rheologic properties of the membranous lining, to breakdown and eliminate the contained microorganisms, biofilm or abiotic toxins adhering to the membranes and coating any implanted device in the middle ear, to normalize surface tension and passive closing pressure, facilitating mucociliary clearance through the restored Eustachian tube orifice into the nasopharynx. The products are then swallowed and arrive in the stomach, where the endogenous enzymes and HCL of the stomach inactivate and digest and any residual microorganisms or proteinaceous products.

The exemplary embodiment is a composition with antioxidant and anti-infective properties that reduce inflammatory reactions of the middle ear which include otitis media (OM), that break down the surface accumulation of biofilm and viscous mucous filling the middle ear cavity of a "glue ear" or otitis media with effusion (OME), to normalize the eustachian tubal function and mucociliary rheologic properties and support healing of middle ear tissues and tympanic membrane defects.

If a tympanic membrane rupture has occurred, as a complication or from specific trauma, the method of the delivery of the exemplary embodiment is modified for the maximum therapeutic effect of supporting healing of the damaged tympanic membrane. This is accomplished by the application of solid, porous or absorbable implanted devices or sculptured to the anatomical defect of the tympanic membrane and implanted under direct visualization employing a surgical microscope. A non-porous device or tube may be implanted for the delivery of the novel embodiment. The implanted device serves as a conduit through which the embodiment is administered via the external ear canal on a scheduled program for continuous availability of the composition of the exemplary embodiment to support tissue healing by pre-collagen formation and re-epithelization cardinal to middle ear functions.

FURTHER SELECTED CASE STUDIES

Example A

DP: A two-year old boy was seen because of multiple earaches. Antibiotics have not been helpful. After several infections his left ear drained. He was treated with Zythromax by his pediatrician. The infection recurred. He was treated with Augmentin. It occurred again, he was treated with an injection of Rocephin antibiotic in both thighs. He was referred to an otolaryngologist who identified a left ear canal fungus infection. The culture obtained was reported as a heavy grown of pseudomonas aeruginosa. He was treated with antifungal otic drops. His examination revealed a left ear canal infection. This was treated. On return examination he demonstrated bilateral negative middle ear pressure. He was treated with the embodiment of L-Ascorbic acid 5% in aqueous saline solution applied as a nasal spray.

Over the next month, his ears cleared and middle ear pressure was within normal limits. His recovery was interrupted by an upper respiratory infection. After his recovery, he continued with the embodiment administered topically to the nasal mucosa. One month later, examination indicated that there was no evidence of any middle ear infection or fluid and the Eustachian Tube function was normal.

Example B

This 75 year old female had a history of bilateral tympanic membrane perforations in 1984. In 1984 she had a cholesteatoma of the left ear removed with good healing of the tympanic membrane. She had a right tympanoplasty with a fascia graft in 1989 with closure of the tympanic membrane perforation. Over the years she's had occasional right middle ear infections. In March 2007 she had a severe right middle ear infection with drainage. Culture report revealed the microorganism *Corynebacterium*. The appropriate embodiment in the composition, L-Ascorbid acid, 5% wt/vol in physiologic saline and vehicle most effective to achieve the curative results were administered in a topical solution, delivered trans canal through the tympanic membrane perforation to the middle ear space, two times a day. The drainage was completely eliminated in five days with no further signs of infection.

Example C

VM. A 76 year-old retired psychologist, with a history of middle ear infections since age 14. She was seen because of chronic right mastoiditis with a total tympanic with recurrent drainage. She had experienced ear infections since childhood and had bilateral tympano-mastoid surgery several times as a younger woman. Postoperatively she had a bilateral hearing loss and a right total tympanic membrane perforation, mastoid and right middle ear drainage which cultured bacteria and/or fungus intermittently. She was treated with topical antibiotics, antifungal medications, and local cleaning of the mastoid cavity by her surgical specialists. Years ago she was also treated with gentomycin, an ototoxic antibiotic, for a severe kidney infection and suffered further a profound hearing loss in her left ear. Her doctors advised her that surgery could not be performed to repair her right eardrum perforation because of the intractable infection. She was treated with the composition of L-Ascorbic acid, 5% wt/vol in an aqueous solution employed on a porous implanted device within the right middle ear space. The composition was self-administered daily by the patient and a fresh porous implanted device inserted every two-three weeks by her Otologist. After three months the drainage had ceased. She was free of infection and the right eardrum perforation had healed closed.

This disclosed composition in its exemplary embodiment at the predetermined pH level inhibits or destroys the microorganism. The surfactant-like surface tension lowering substance (STLS) properties reduce or disrupt the adherence of the biofilm or abiotic adhesins on the surface of the epithelium of the middle ear, Eustachian tube adnexa, nasal and sinus epithelium. This releases the altered microorganisms from contact with the epithelium. The periciliary fluid and ciliary motility work in concert to transport the foreign matter to the nasopharynx for elimination. As the viscosity of the mucous blanket decreases and the ciliary system resumes beating, the blanket transports the microorganisms, organic and abiotic particulate matter from the middle ear chamber cleansing it of contaminants.

The rheologic properties of the composition of the present invention accelerate the breakdown of the toxins and facilitate the elimination of the foreign matter by the mucociliary transport system. The antioxidant properties allow mucous membrane healing to begin and this essential nutrient enables the bioactive process of stimulating fibroblasts and pre-collagen synthesis and healing to take place.

The inability of man to synthesize L-Ascorbic acid is due to the absence of the biochemical step in the liver of his species to convert L-gulonolactone which is required for the biosynthesis of L-ascorbic acid.

Table 1 illustrates the potential bioactive properties of the exemplary embodiments of the present invention and novel method:

TABLE 1

| Embodiment Properties | Bioactive Effects |
| --- | --- |
| Source of Ascorbic acid (AA). | Humans cannot synthesize AA. Exogenous source is required. |
| Method of pH levels | Low pH inhibits the resistance and virulence of microorganisms. Specific pH levels enhance nutrient-tissue metabolic reactions. |
| Epithelial Adherence | AA reduces physical adherence by biofilm and abiotic products. |
| Antioxidant Properties | AA activates metabolites to break down free oxygen radicals. |
| Surfactant Properties | AA has surface tension lowering properties to release the biofilm and toxic products from the host membranes |
| Enzymatic Cofactors | Facilitates pre-collagen formation and strengthens tissue healing. |

For the embodiments disclosed herein, the composition is safe, the methods described are controllable, and therapeutic results observable by the described techniques including the direct topical intranasal application or alternate route of the administration of the invention in the form of drops, nasal spray or aerosol sprays prepared in vials of variable sizes containing the appropriate embodiment in milliliter concentrations delivered according to a predetermined number of metered drops or sprays from non-aerosol pumps, or self contained propellant for aerosol spray, gels or delivered by controlled syringe, catheter, implantable porous or solid devices.

The disclosed embodiments represent an invention that is novel for treatment of the most common forms of middle ear disease disorders or conditions. It provides an exogenous essential nutrient which man cannot synthesize but must ingest. The proper pH level of the composition can potentiate its biochemical antimicrobial properties to inhibit the growth of microorganisms. The composition exhibits antioxidant properties to breakdown biofilm and abiotic toxins, and reduces epithelial adherence. The composition of the disclosed embodiments includes an essential cofactor in the production of precollagen for tissue healing. All of the compositions disclosed herein offer a much safer and broader treatment for the inflammatory diseases than the newer higher potency antibiotics with increased risk of ototoxic side effects and major complications reported by current medical experts.

Further, the desired therapeutic response is provided by direct topical intranasal topical administration of the invention in the form of drops, nasal spray or aerosol sprays prepared in vials of variable sizes containing the composition of the disclosed embodiments in milliliter concentrations delivered according to a predetermined number of metered drops or sprays from non-aerosol pumps, rinse, douche or self contained propellant for aerosol spray, gels or delivered by controlled syringe, catheter, implantable solid, porous, absorbable, or similar device.

The invention provides a composition and method of treatment for alleviating the symptoms of the Patulous Eustachian tube syndrome and related similar luminal Eustachian Tube Incompetence disorders, including interruption of the structural integrity of the Eustachian tube by disease, surgery, trauma or the changes associated with development or aging.

Having now described exemplary embodiments in detail as required by the patent statutes, those skilled in the art will recognize modifications and substitutions to the specific embodiments disclosed herein. Such modifications are within the scope and intent of the present invention as defined in the following claims.

What is claimed is:

1. A method of treating the patulous Eustachian tube syndrome, a severe variant, of Eustachian tube incompetence, comprising:
applying to a person's nasal mucosa a composition of L-Ascorbic acid, in a highly acidic concentration of about 5% to about 20% wt/vol, within a range of about 2.4 to 2.0 pH level, in an aqueous solution, and a pharmaceutically acceptable liquid carrier and delivery system.

2. A method according to claim 1 in which the solution is applied topically to the nasal mucosa by positioning the person's head between 45 to 60 degrees above horizontal and turned 45 to 60 degrees toward an ear affected by patulous Eustachian tube syndrome thereby placing the Eustachian tube stoma lower than the nostril.

3. A method according to claim 1 in which the solution is applied to the middle ear chamber.

4. A method according to claim 2 in which the solution is applied in drops into the nose.

5. A method according to claim 2 in which the solution is applied in a spray into the nose.

6. A method according to claim 2 in which the solution is applied in an aerosol into the nose.

7. A method according to claim 1 in which the solution is applied topically via an ET catheter to the nasopharyngeal stoma of the Eustachian tube.

8. A method according to claim 3 in which the solution is applied to the middle ear employing a syringe and needle.

9. A method according to claim 3 in which the solution is applied to the middle ear employing a trans-tympanic membrane puncture.

10. A method according to claim 3 in which the solution is applied to the middle ear employing a myringotomy.

11. A method according to claim 3 in which the solution is delivered by employing an implanted device to or in the middle ear chamber.

12. A method according to claim 3 in which a porous device is implanted within a defect of the tympanic membrane or the middle ear chamber.

13. A method according to claim 11 in which the solution is applied to the porous device.

14. A method according to claim 1 in which the liquid carrier is distilled water.

15. A method according to claim 1 in which the L-ascorbic acid is L-3-keto threo hexuronic acid lactone and the solution has a pH in the range of about 2.2 pH to about 2.0 pH level.

16. A method according to claim 1 in which the L-Ascorbic acid is present in the carrier at a concentration from about 10% to about 20% wt./volume.

17. A method according to claim 8 in which the solution further comprises distilled water.

18. A method according to claim 1 in which the composition includes an antioxidant.

19. A method according to claim 18 wherein the antioxidant is a flavone, bioflavonoid, in a concentration of about 0.1 to 0.5% wt/vol.

20. A method according to claim 18 wherein the antioxidant is Tocopherol.

21. A method according to claim 18 wherein the antioxidant is water solubilized vitamin E (alpha-tocopherol) in a concentration of about 500 to 1,000 i.u./100 m.

* * * * *